(12) United States Patent
Ratto et al.

(10) Patent No.: US 11,730,391 B2
(45) Date of Patent: Aug. 22, 2023

(54) HANDHELD BREATH ANALYTE DETECTION DEVICE

(71) Applicant: Readout, Inc., St. Louis, MO (US)

(72) Inventors: Timothy V. Ratto, San Mateo, CA (US); Matthew V. Ratto, East York (CA)

(73) Assignee: Readout, Inc., St. Louis, MO (US)

( * ) Notice: Subject to any disclaimer, the term of this patent is extended or adjusted under 35 U.S.C. 154(b) by 0 days.

(21) Appl. No.: 17/851,792

(22) Filed: Jun. 28, 2022

(65) Prior Publication Data

US 2023/0084590 A1    Mar. 16, 2023

Related U.S. Application Data (63) Continuation of application No. 17/031,842, filed on Sep. 24, 2020, now Pat. No. 11,375,920, which is a
(Continued)

(51) Int. Cl.
*A61B 5/08*           (2006.01)
*G01N 33/497*      (2006.01)
(Continued)

(52) U.S. Cl.
CPC ............. *A61B 5/082* (2013.01); *A61B 5/742* (2013.01); *G01N 33/497* (2013.01); *A61B 5/091* (2013.01);
(Continued)

(58) Field of Classification Search
CPC ................. G01N 33/64; G01N 33/497; G01N 2033/4975; G01N 2033/4977; G01N 2001/2244; A61B 5/097; Y10S 436/90
See application file for complete search history.

(56) References Cited

U.S. PATENT DOCUMENTS

| 5,071,769 A | 12/1991 | Kundu et al. |
| 6,467,333 B2 | 10/2002 | Lewis et al. |

(Continued)

FOREIGN PATENT DOCUMENTS

| EP | 2878949 A1 | 6/2015 |
| JP | 2014-117429 A | 6/2014 |

(Continued)

OTHER PUBLICATIONS

International Search Report and Written Opinion, PCT Application No. PCT/US2019/039623, dated Nov. 7, 2019, 12 pages.
(Continued)

*Primary Examiner* — Nathaniel J Kolb
(74) *Attorney, Agent, or Firm* — Fenwick & West LLP (57) ABSTRACT

A breath analyte device includes a breath volume in fluid communication with a sampling volume. The device also includes a sampling sensor configured to generate a breath signal that varies in response to changes in gas pressure (e.g., sound waves) in the breath volume and one or more analyte sensors configured to generate one or more analyte signals that vary in response to a concentration of one or more target analytes present in the sampling volume. A control unit is configured to determine a time at which to measure the concentration of target analytes in the sampling volume based on the breath signal and measure the concentration of the target analytes based on the analyte signals at the determined time. The device may also include a pump configured to motivate gas from the breath volume into the sampling volume prior to measuring the concentration of the target analytes.

20 Claims, 7 Drawing Sheets

Related U.S. Application Data continuation-in-part of application No. 16/863,991, filed on Apr. 30, 2020, now Pat. No. 11,399,737, which is a continuation of application No. 16/455,505, filed on Jun. 27, 2019, now Pat. No. 10,682,072.

(60) Provisional application No. 62/695,882, filed on Jul. 10, 2018.

(51) Int. Cl.
*A61B 5/00* (2006.01)
*A61B 5/091* (2006.01)

(52) U.S. Cl.
CPC ............ *G01N 2033/4975* (2013.01); *G01N 2033/4977* (2013.01)

(56) References Cited

U.S. PATENT DOCUMENTS

| | | | |
|---|---|---|---|
| 6,609,068 | B2 | 8/2003 | Cranley et al. |
| 6,841,391 | B2 | 1/2005 | Lewis et al. |
| 7,034,943 | B1* | 4/2006 | Moeckli ............ C07K 14/705 356/423 |
| 7,076,371 | B2 | 7/2006 | Fu |
| 7,352,465 | B2 | 4/2008 | Fay et al. |
| 7,364,551 | B2 | 4/2008 | Allen et al. |
| 7,820,108 | B2 | 10/2010 | Lampotang et al. |
| 7,950,271 | B2 | 5/2011 | Novak et al. |
| 8,519,446 | B2 | 8/2013 | Dass et al. |
| 8,932,525 | B1 | 1/2015 | Ahmad et al. |
| 9,035,777 | B2 | 5/2015 | Bangera et al. |
| 9,164,052 | B1 | 10/2015 | Speer et al. |
| 9,183,757 | B2 | 11/2015 | Yamada et al. |
| 9,188,579 | B2 | 11/2015 | Shen et al. |
| 9,424,396 | B2 | 8/2016 | Bangera et al. |
| 9,456,749 | B2 | 10/2016 | Roeck et al. |
| 9,518,991 | B2 | 12/2016 | Ahmad et al. |
| 2005/0083527 | A1 | 4/2005 | Flaherty et al. |
| 2005/0233459 | A1 | 10/2005 | Melker et al. |
| 2007/0172424 | A1 | 7/2007 | Roser |
| 2010/0255598 | A1 | 10/2010 | Melker et al. |
| 2013/0165806 | A1 | 6/2013 | Wondka et al. |
| 2013/0305808 | A1* | 11/2013 | Yoo ............... G01N 33/4972 73/23.3 |
| 2014/0165698 | A1* | 6/2014 | Mochizuki ........ G01N 33/4972 73/23.3 |
| 2014/0276100 | A1 | 9/2014 | Satterfield et al. |
| 2014/0366610 | A1 | 12/2014 | Rodriguez |
| 2014/0377877 | A1 | 12/2014 | Bürgi et al. |
| 2015/0032019 | A1 | 1/2015 | Acker et al. |
| 2016/0327532 | A1 | 11/2016 | Bather et al. |
| 2016/0331272 | A1 | 11/2016 | Ahmad et al. |
| 2017/0224250 | A1* | 8/2017 | Mokuo ............... A61B 5/097 |
| 2017/0303822 | A1* | 10/2017 | Allsworth .......... A61B 5/097 |
| 2017/0303823 | A1* | 10/2017 | Allsworth .......... A61B 10/00 |
| 2018/0003660 | A1* | 1/2018 | Tayebi .............. G01N 33/0047 |
| 2018/0017569 | A1 | 1/2018 | Melker et al. |
| 2018/0146888 | A1 | 5/2018 | Güntner et al. |
| 2019/0025271 | A1 | 1/2019 | Yan et al. |

FOREIGN PATENT DOCUMENTS

| | | |
|---|---|---|
| JP | 2015-503962 A | 2/2015 |
| JP | 2015-102531 A | 6/2015 |
| JP | 2017-067539 A | 4/2017 |
| WO | WO 2006/102064 A2 | 9/2006 |

OTHER PUBLICATIONS

United States Office Action, U.S. Appl. No. 16/455,505, filed Oct. 11, 2019, 14 pages.
Extended European Search Report, European Patent Office Application No. 19833647.1, dated Jun. 3, 2022, 12 pages.
Japanese Office Action, Japan Patent Office Patent Application No. 2021-523552 2021-523552, dated Apr. 4, 2023, 12 pages.

* cited by examiner

HANDHELD BREATH ANALYTE DETECTION DEVICE

CROSS REFERENCE TO RELATED APPLICATIONS

This application is a continuation of U.S. patent application Ser. No. 17/031,842, filed Sep. 24, 2020, which is a continuation-in-part of U.S. patent application Ser. No. 16/863,991, filed Apr. 30, 2020, which is a continuation of U.S. patent application Ser. No. 16/455,505, filed Jun. 27, 2019, which claims the benefit under 35 U.S.C. § 119(e) of U.S. Provisional Patent Application No. 62/695,882, filed Jul. 10, 2018, all of which are incorporated by reference.

BACKGROUND

1. Technical Field

The subject matter described relates generally to chemical detection and, in particular, to devices that detect specific analytes in exhaled breath.

2. Background Information

Exhaled breath contains many analytes that are non-invasive indicators of various physiological conditions. Because breath may be monitored non-invasively, breath acetone measurement is attractive as a tool for monitoring lifestyle modifications that impact health such as dietary adherence and weight-loss. For example, breath acetone correlates with metabolic status in humans and can be used to quantify adherence to a reduced carbohydrate/calorie diet, exercise and, for diabetics, progression towards a life-threatening condition called ketoacidosis.

To this end, multiple entities have attempted to produce breath acetone products that consumers can use at home to measure and track breath acetone. However, existing approaches suffer from deficiencies that reduce the accuracy and reproducibility of the breath acetone measurement. Furthermore, existing approaches generally struggle to distinguish between acetone and other analytes in human breath. Consequently, the value of existing solutions (both commercially and in providing health benefits) is limited.

SUMMARY

A breath analyte device uses a sampling sensor to determine when to sample a user's breath for detection of one or more target analytes. A sample of the user's breath is drawn into a sampling volume (e.g., a flow cell) that includes one or more analyte sensors at the determined time. The analyte sensors may be chosen based on their response to the target analytes and other analytes typically present in breath. The device includes a control unit configured to determine the amount of the target analytes present in the user's breath using the output from the analyte sensors.

In various embodiments, the sampling sensor is an audio sensor (e.g., a microphone). The device samples the user's alveolar breath by identifying the end portion of the user's breath from the output from the audio sensor. The control unit may identify the beginning of a breath by an increase in the output from the audio sensor relative to a base level. The output from the audio sensor will typically increase to a peak value and then begin to decrease through the breath. The end portion of the breath may begin when the output from the audio sensor drops below a threshold defined relative to the peak value and end when the output returns to the base level. Sampling alveolar breath may be referred to as "end-of-breath" or "late-breath" sampling.

In one embodiment, a breath analyte device detects the presence and concentration of acetone and hydrogen in a user's breath. The device includes a breath volume for receiving gas exhaled from a user and a flow cell in fluid communication with the breath volume. A microphone is in fluid communication with the breath volume. Acetone and hydrogen sensors are in fluid communication with the flow cell. The acetone sensor may be selected to provide a good signal-to-noise ratio in its response to acetone versus hydrogen and other breath analytes. The hydrogen sensor may be selected to have good signal-to-noise ratio relative to other breath analytes. A control unit detects the approach of the end of the user's breath from audio data generated by the microphone and activates a pump to move a portion of the user's breath from the breath volume to the flow cell. The control unit then generates a measurement of the amounts of acetone and hydrogen in the user's breath from the output of the analyte sensors.

The acetone sensor may be refreshed between each measurement to improve consistency and accuracy. For example, when the breath acetone device is turned on or woken up, the flow cell may be cleared by the pump and the acetone sensor heated to an elevated temperature to burn off adsorbed chemicals and generate negatively charged oxygen species at the active surface. The pump may be activated again (or it may remain on) to remove desorbed chemicals from the flow cell and the acetone sensor is maintained at an elevated temperature sufficient to prevent significant adsorption of chemicals. In response to user input requesting a measurement, the temperature of the acetone sensor is reduced to a sampling temperature.

The combination of end-of-breath sampling and analyte sensor selection may provide high accuracy breath acetone and hydrogen measurements without the need for complex, bulky, or expensive equipment. Consequently, the breath analyte device may be handheld and operated by users without specialized medical training. The device may also be relatively low-cost, making it attractive for a wide range of applications, from monitoring potentially life-threatening diseases to encouraging adherence to fitness programs. The breath analyte device is also non-invasive, making it preferable to users over other diagnostic techniques, such as blood tests.

BRIEF DESCRIPTION OF THE DRAWINGS

The figures and following description describe certain embodiments by way of illustration only. One skilled in the art will readily recognize from the following description that alternative embodiments of the structures and methods may be employed without departing from the principles described. Wherever practicable, similar or like reference numbers are used in the figures to indicate similar or like functionality.

DETAILED DESCRIPTION

The accurate and reproducible measurement of breath analytes has several challenges. These challenges include sample timing, sensor sensitivity, analyte differentiation. These challenges are particularly pertinent for handheld or otherwise portable devices intended for use by individuals without specialized training. Portability places restraints on the size and weight of components that may be used as well as the extent to which testing conditions can be controlled. Similarly, operation by untrained users limits the extent to which test conditions can be controlled and managed. Commercial concerns may also place limits on the components used.

With regard to sample timing, the concentrations of analytes in a human breath vary according to the depth of exhalation. Thus, accuracy and reproducibility of breath analyte measurement can be improved by consistently sampling from the portion of the breath cycle with a high relative concentration of the target analyte. For example, in the case of acetone, the beginning of a breath contains the lowest concentration due to dilution with outside air and the end of the breath contains the highest concentration due to the highest degree of transfer from the blood in the lungs and airways. Therefore, end-of-breath sampling may provide improved accuracy and reproducibility.

In controlled environments, such as hospitals and other medical facilities, the end of a breath may be detected based on the periodic nature of breathing having a reasonably constant frequency (at least over the time scale of tens of breaths). However, with portable devices used by individuals at locations of their choice, determining the appropriate portion of a breath to sample from a single breath (or small number of breaths) is more challenging. In such cases, earlier breaths cannot be used to determine a breathing pattern (e.g., frequency of breaths and the relative length of a breathing in versus breathing out portion of the cycle). Furthermore, measurements of breath analytes are often determined by integrating a sensor signal over a time period that is significantly longer than a typical breath. This is trivial if a sample is collected in a vessel (e.g., a sample tube) for later analysis, but creates additional challenges for devices that analyze the sample at collection time to provide almost immediate results.

With regard to sensor sensitivity, the concentration of breath analytes can vary over a relatively large range. For example, acetone can range from ~100 parts per billion (ppb) to >100 parts per million (ppm). The response of the analyte sensor to the target analyte throughout the range that it is likely to appear in human breath can significantly impact accuracy and reproducibility.

With regard to analyte differentiation, human breath contains a variety of chemical analytes. Typically, sensors are sensitive to several analytes in human breath. For example, many acetone sensors also respond to hydrogen, carbon monoxide, alcohols, isoprene, and/or ammonia. Different sensors have different ratios of sensitivity between acetone and these other analytes. Thus, accounting for expected sensor responses due to other analytes may significantly improve the accuracy and reproducibility of measurements of target analytes. Furthermore, including sensors for two or more target analytes and calibrating for correlated responses between the sensors for the target analytes may further improve accuracy.

In the description that follows, various principles are described with reference to an example device that measures the concentration of acetone and hydrogen for convenience. This should not be taken as limiting the scope of this disclosure to such devices. Rather, it should be understood that many of these principles are applicable to breath analyte devices configured to detect other analytes and combinations of analytes.

Example Breath Acetone and Hydrogen Device

Figure 1:
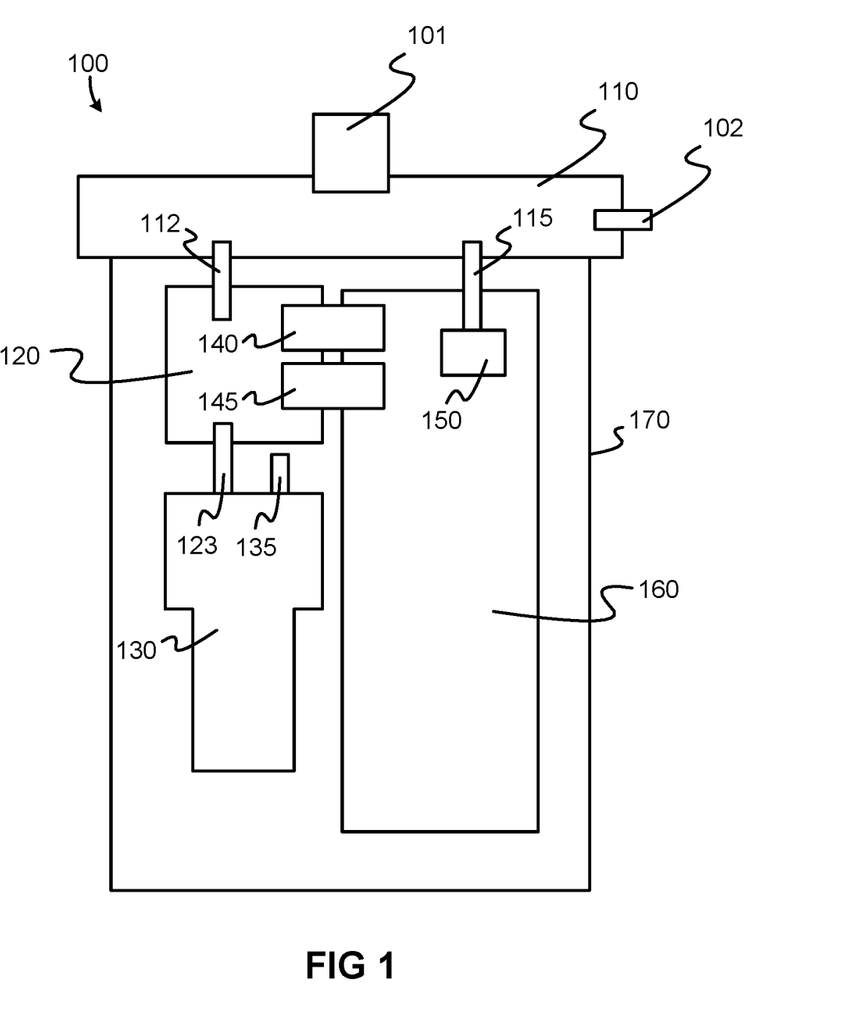
FIG. 1 is a schematic diagram of a breath analyte device, according to one embodiment.

FIG. 1 illustrates one embodiment of a breath analyte device 100 that measures the acetone and hydrogen concentrations. In the embodiment shown, the device 100 includes a breath volume 110, a flow cell 120, a pump 130, an acetone sensor 140, a hydrogen sensor 145, a sampling sensor 150, and a control unit 160, all within a housing 170. Although the embodiment shown in FIG. 1 has an acetone sensor 140 and a hydrogen sensor 145, it should be recognized that sensors for a wide range of different or additional target analytes may be included in the breath analyte device 100. Furthermore, some embodiments may include sensors for measuring other properties, such as temperature, relative humidity, ionization, etc.

The breath volume 110 is fluidly connected to the exterior environment by an input aperture 101 in the housing (e.g., a mouthpiece) and an output aperture 102 (e.g., a vent or valve). The breath volume 110 is fluidly connected to the flow cell 120 via a flow conduit 112. The sampling sensor 150 is fluidly connected to the breath volume 110 via a sampling conduit 115. The pump 130 is fluidly connected to the flow cell 120 via a pump conduit 123. The pump 130 may also be fluidly connected to the exterior environment by a vent 135. In other embodiments, the breath analyte device 100 may include different or additional elements.

The breath volume 110 generally forms a conduit through which air exhaled by a user may pass through. A user may press their lips around the input aperture 101 and exhale into the breath volume. The input aperture 101 may be part of a mouthpiece designed for the user to comfortably form a seal around the aperture with their lips and blow in the breath volume. The exhaled air may then freely or with restriction pass from the input aperture 101, through the breath volume 110, and out of the output aperture 102. The breath volume 110 may be configured in any shape and size. For example, the breath volume 110 may comprise a generally cylindrical shape, rectangular prism shape, or any other shape. A breath volume 110 may be made from a substantially rigid and/or flexible material or combination of materials. In various embodiments, the breath volume 110 has a volume of approximately 5 to 200 milliliters, although larger and smaller sizes may be used.

The flow cell 120 includes a chamber or conduit configured for directing gas towards and away from two or more analyte sensors (in the example shown, an acetone sensor 140 and a hydrogen sensor 145). The flow cell 120 may be configured in any size and shape and may be made from a substantially rigid and/or flexible material or combination of materials. In various embodiments, the flow cell 120 has a volume of approximately 2 to 200 milliliters, such as 2 to 50 milliliters, although larger and smaller sizes may be used. In the embodiment shown in FIG. 1, the flow cell 120 is in fluid communication with the breath volume 110 via a flow conduit 112. The flow conduit 112 is a passageway, such as a tube, that allows gas to flow between the breath volume 110 and flow cell 120. In other embodiments, the flow cell 120 may be coupled to the breath volume 110 in other ways.

The sampling sensor 150 gathers data that the control unit 160 can use to determine an appropriate time to sample the user's breath. The sampling sensor 150 outputs a sampling signal that varies in response to one or more variables that are indicative of the stage of the user's breath. In various embodiments, the sampling sensor 150 is an audio sensor that detects perturbations in gas pressure in the vicinity of the device 100 (e.g., in the breath volume 110) that are indicative of the approach of the end of a user's breath. In the embodiment shown in FIG. 1, the audio sensor 150 is in fluid communication with the breath volume 110 via the sampling conduit 115. The sampling conduit 115 is a passageway, such as a tube, that allows gas to flow between the breath volume 110 and the audio sensor 150.

In one embodiment, the audio sensor 150 is a microphone configured to pick up or record audio information. The microphone may include any acoustic-to-electric transducer or sensor that converts sound waves in the surrounding gas into an electrical signal that it provides to the control unit 160. Example types of microphone include electromagnetic induction microphones (dynamic microphones), capacitance change microphones (condenser microphones), and piezoelectricity microphones (piezoelectric microphones). The output from the microphone may be passed through one or more frequency filters to remove components of the audio spectrum that do not correlate strongly with the approach of the end of the user's breath. For example, a high pass filter may be applied to remove frequencies below approximately one kilohertz (kHz) and/or a low pass filter may be applied to remove above approximately ten kHz.

In alternative embodiments, the sampling sensor 150 may comprise a pressure sensor a which may be configured to record air pressure information from the environment around the device 100 and/or within the breath volume 110. Example pressure-type sampling sensors 150 include silicon MEMS strain gauge sensors, piezoresistive silicon pressure sensors, analog output pressure transducer sensors, remote wireless pressure transducers, harsh media pressure sensors, digital output absolute pressure sensors, IsoSensor pressure sensors, solid state pressure sensors, or any other type of air pressure sensing method or device.

The pump 130 is configured to motivate air between the breath volume 110 and the flow cell 120. The pump 130 may include any device configured to cause, motivate, or direct air flow. Example pumps 130 include a rotating arrangement of vanes or blades capable of moving air, such as a rotary vane pump, a diaphragm pump, a piston pump, a scroll pump, a screw pump, a Wankel pump, an external vane pump, a roots blower or booster pump, a multistage roots pump, a blower fan, a vane pump, axial-flow fans, centrifugal fans, cross-flow fans, bellows, Coandă effect air movers, electrostatic air movers, or any other device or method capable of moving air.

In various embodiments, when the output from the audio sensor 150 indicates the end of the user's breath is approaching, the control unit 160 activates the pump such that a portion of the user's breath is pumped from the breath volume 110 to the flow cell 120. In the embodiment shown in FIG. 1, the pump 130 pulls gas out of the flow cell 120 via the pump conduit 123, which is a passageway, such as a tube, that allows air to flow between the pump 130 and flow cell 120. The removal of gas results in a negative pressure differential between the flow cell 120 and the breath volume 110. Consequently, gas (e.g., the user's breath) moves from the breath volume 110 into the flow cell 120. In other embodiments, the pump 130 may create or generate an increase in pressure in the flow cell 120 which may cause gas within the flow cell 120 to be replaced by gas from outside of the flow cell 120 (e.g., fresh air).

In embodiments that include a vent 135 in fluid communication with a pump 130, the vent 135 may provide a source of fresh air for the pump 130 to provide or exchange with the flow cell 120. The vent 135 is a passageway, such as a tube, which allows air to flow into and/or out of the pump 130. For example, for pumps 130 that only pull (as opposed to pull and also push), the vent 135 may be used as a source of fresh air with which to clear the flow cell 120 after a breath measurement to prepare the device 100 for the next measurement. Alternatively, a pump 130 that can both push and pull may be used. In this case, the pump 130 first pulls the breath sample into the flow cell 120 and then, after the measurement, pushes the breath sample back into the breath volume 110. Thus, the vent 135 may be omitted.

The acetone sensor 140 generates an output acetone signal that varies with the concentration of acetone in gas to which it is exposed. For example, the output may be an electrical signal that increases with acetone concentration at an active surface of the sensor 140. In one embodiment, the acetone sensor 140 includes a metal-oxide sensor, such as a tungsten oxide or zinc oxide sensor (e.g., the SB-33 or SP-33 sensors provided by Nissha FIS). The metal oxide sensor may include additional metal oxides. For example, a tungsten oxide sensor may be doped with gold, platinum, iron, silicon, gadolinium, holmium, yttrium and/or other rare earth materials.

The acetone sensor 140 may be selected to be significantly more responsive to acetone than other analytes that may be present in breath. In some embodiments, the acetone sensor 140 is at least fifty times more sensitive to acetone than one or more of: hydrogen, alcohols, carbon monoxide, ammonia, methane, or other chemicals commonly found in exhaled breath. In other embodiments, the acetone sensor 140 is at least twenty times more sensitive to acetone than one or more of: hydrogen, alcohols, carbon monoxide, ammonia, methane, or other chemicals commonly found in exhaled breath.

The hydrogen sensor 145 generates an output hydrogen signal that varies with the concentration of hydrogen in gas to which it is exposed. For example, the output may be an electrical signal that increases with hydrogen concentration in gas in the flow cell 120. In one embodiment, the hydrogen sensor 145 includes an electrochemical sensor, such as the 4YHT from City Technology or the H2/M-1000, H2/CA-1000, or H2/C-2000 from Membrapor.

The control unit 160 is a computing device configured to control operation of and/or receive data from other components of the breath analyte device 100. In one embodiment, the control unit 160 is coupled (e.g., optically or electrically) to the pump 130 and controls its operation. The control unit 160 is also coupled (e.g., optically or electrically) to the acetone sensor 140, hydrogen sensor 145, and audio sensor 150. The control unit 160 receives and processes data from the acetone sensor 140, hydrogen sensor 145, and audio sensor 150. The control unit 160 may also control one or more I/O interfaces of the device 100. Various embodiments of the control unit 160 are described in greater detail below, with reference to FIG. 4.

Figure 2:
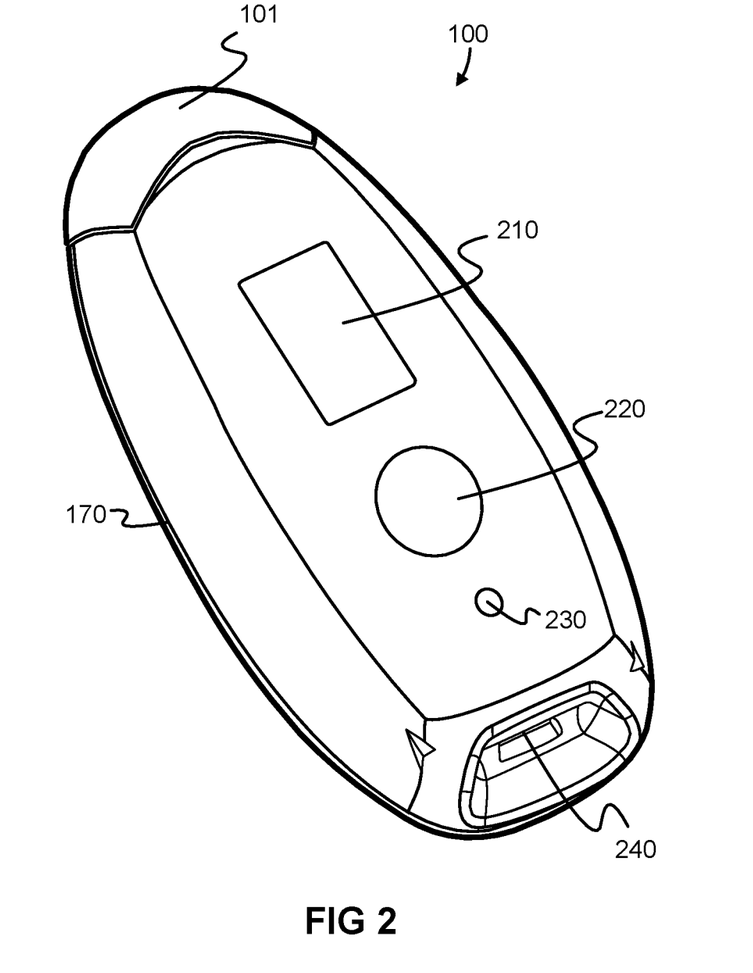
FIG. 2 is perspective view of the exterior housing of the breath analyte device of FIG. 1, according to one embodiment.

FIG. 2 illustrates the exterior of the example breath analyte device 100 shown in FIG. 1. The housing 170 may be configured in any shape and size, such as an ovoid shape, rectangular prism shape, triangular prism shape, or any other shape. In one embodiment, the housing has a maximum length between five and twenty centimeters, a maximum width between two and ten centimeters, and a maximum depth between one and three centimeters. Thus, the breath analyte device 100 may be handheld and easily stored in a user's pocket or bag.

In some embodiments, a housing 170 may be made from or may comprise a substantially rigid material, such as steel alloys, aluminum, aluminum alloys, copper alloys, other types of metal or metal alloys, ceramics such as alumina, porcelain, and boron carbide, earthenware, natural stone, synthetic stone, various types of hard plastics, such as polyethylene (PE), Ultra-high-molecular-weight polyethylene (UHMWPE, UHMW), polypropylene (PP) and polyvinyl chloride (PVC), polycarbonate, nylon, Poly(methyl methacrylate) (PMMA) also known as acrylic, melamine, hard rubbers, fiberglass, carbon fiber, resins, such as epoxy resin, wood, other plant based materials, or any other material including combinations of materials that are substantially rigid. In further embodiments, a housing 170 may be made from or may comprise a flexible material such as natural and/or synthetic rubber material such as latex rubber, forms of the organic compound isoprene, Polyacrylate Rubber, Ethylene-acrylate Rubber, Polyester Urethane, flexible plastics, such as high-density polyethylene (HDPE), polyvinyl chloride (PVC), polypropylene (PP), Polystyrene (PS), Polycarbonate (PC), low density polyethylene (LDPE), or any other flexible material including combinations of materials.

The breath analyte device 100 may include one or more I/O interfaces on the exterior of the housing 170. In the embodiment shown in FIG. 2, the device 100 has a display 210, an action button 220, a menu button 230, and a Universal Serial Bus (USB) port 240. The display 210 presents information such as instructions and results to users. The action button 220 may transition the device from an off (or sleeping) state to an on (or ready) states, initiate a measurement, and/or select menu options (e.g., an option currently highlighted on the display 210). The menu button 230 may enable user-selection if various options (e.g., pressing the menu button 230 a first time may cause a menu to be displayed on the display 210 with a first option highlighted and pressing it additional times may cycle through highlighting of additional options). The USB port 240 provides an interface via which data can be uploaded to and downloaded from the device 100. For example, breath acetone and hydrogen measurements may be downloaded to a computer for aggregation and analysis and software updates may be uploaded to the device 100. In other embodiments, the device 100 may include different or additional I/O interfaces. Furthermore, the functionality may be distributed between I/O interfaces in a different manner than described.

Figure 3:
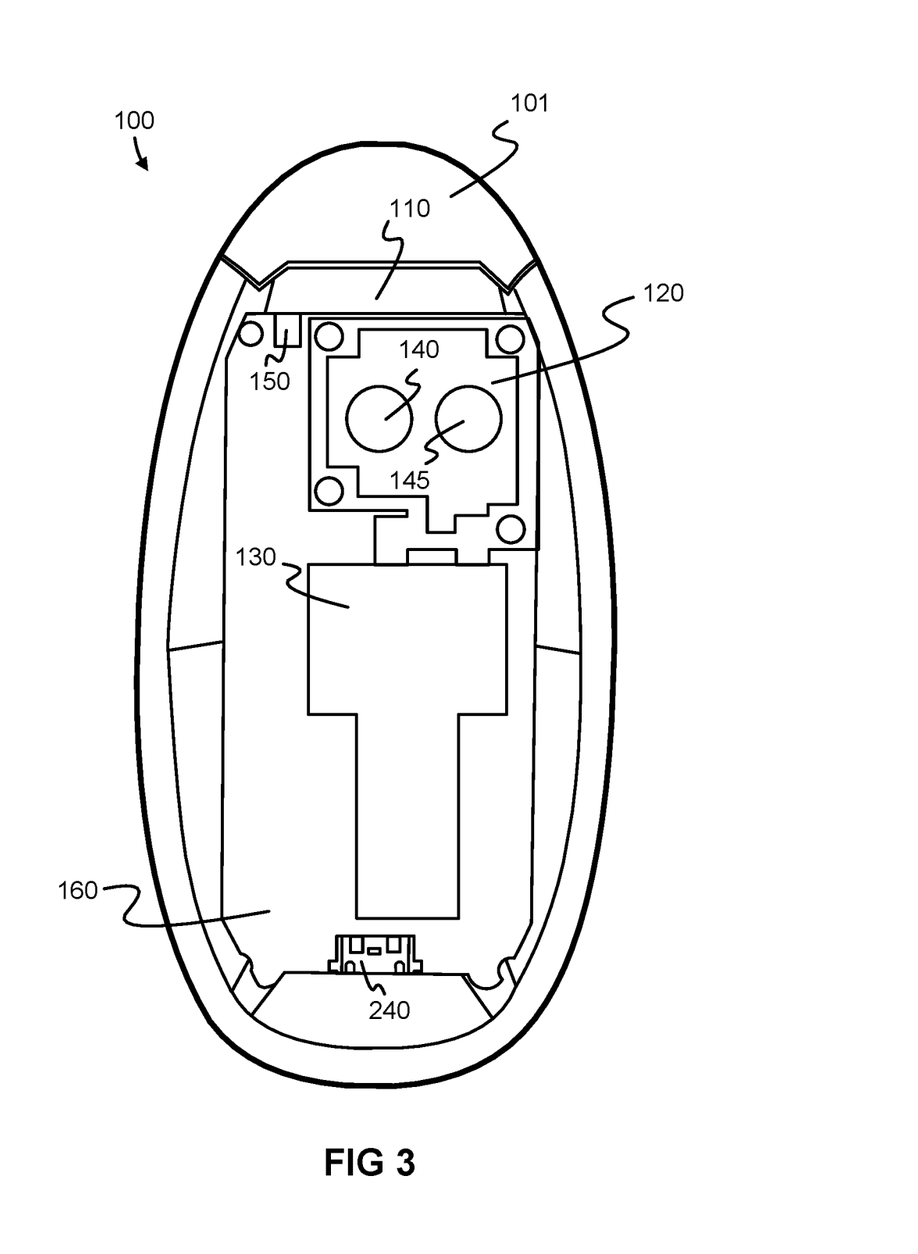
FIG. 3 is perspective view of the interior of the breath analyte device of FIG. 1, according to one embodiment.

FIG. 3 illustrates the interior of the example breath analyte device 100 shown in FIG. 1. In the embodiment shown in FIG. 3, the flow cell 120, pump 130, acetone sensor 140, hydrogen sensor 145, and sampling sensor 150 are mounted on a printed circuit board of the control unit 160. This configuration may be convenient for manufacture as it makes coupling the control 160 to the other components (e.g., electrically) relatively straight forward. The compact arrangement also enables the breath analyte device 100 to be relatively small to conveniently fit in a user's hand, pocket, bag, etc.

Example Control Unit

Figure 4:
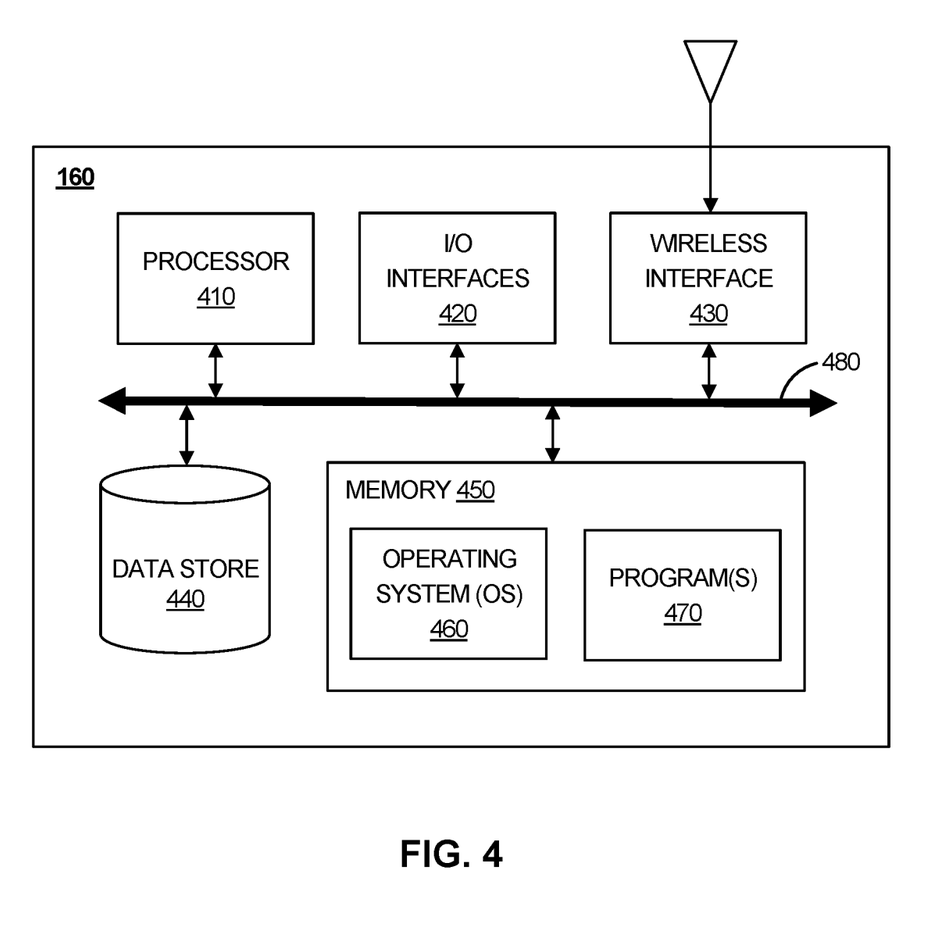
FIG. 4 is a block diagram illustrating a computer-based control unit of a breath analyte measurement device, according to one embodiment.

FIG. 4 illustrates one embodiment of the control unit 160 of a breath analyte device 100. In the embodiment shown in FIG. 4, the control unit 160 includes a processor 410, I/O interfaces 420, a wireless interface 430, data store 440, and a memory 450. The memory 450 includes an operating system (OS) 460 and one or more programs 470. It should be appreciated that FIG. 4 depicts an example of a control unit 160 in an oversimplified manner, and a practical embodiment may include additional components or elements and suitably configured processing logic to support known or conventional operating features that are not described in detail herein.

The components of a control unit 160 and other elements of the breath analyte device 100 (e.g., the pump 130, acetone sensor 140, hydrogen sensor 145, and audio sensor 150) may be communicatively coupled via a local interface 480. The local interface 480 can be, for example, one or more buses or other wired or wireless connections, integrated circuits, etc. The local interface 480 can have additional elements, which are omitted for simplicity, such as controllers, buffers (caches), drivers, repeaters, and receivers, among many others, to enable communications. Further, the local interface 480 may include address, control, and/or data connections to enable appropriate communications among the other components.

The processor 410 is one or more hardware devices for executing software instructions. The processor 410 can be any custom made or commercially available processor, such as a central processing unit (CPU), an auxiliary processor among several processors, a semiconductor-based microprocessor (in the form of a microchip or chip set), or generally any device for executing software instructions. When in operation, the processor 410 is configured to execute software stored within the memory 450, to communicate data to and from the memory 450, and otherwise control operations of the device 100 pursuant to the software instructions. In one embodiment, the processor 410 is optimized for use in a handheld device. For example, the processor 410 may be configured for low power consumption.

The I/O interfaces 420 can be used to input and/or output information and/or power to the device 100. In some embodiments, the I/O interfaces 420 may include one or more input interfaces, including turnable control knobs, depressible button type switches, key pads, slide type switches, dip switches, rocker type switches, rotary dial switches, numeric input switches, or any other suitable input which a user may interact with to provide input. The I/O interfaces 420 may also include one or more information displays, including light emitting diode (LED) displays, LCD displays, speakers, or any other suitable devices for outputting or displaying information. The I/O interfaces 420 can also include one or more data output ports, including USB ports, serial ports, parallel ports, small computer system interface (SCSI) ports, and the like. Example I/O interfaces include the display 210, action button 220, menu button 230, and USB port 240 shown in FIG. 2. In one embodiment, the breath acetone device 100 includes rechargeable power source (e.g., a battery or capacitor) and an I/O interface 420 (e.g., the USB port 240) may be used to charge the power source.

The wireless interface 430 (if included) enables wireless communication to an external access device or network. The wireless interface 430 may include a wireless communication receiver and/or a wireless communication transmitter. In one embodiment, the wireless interface 430 operates on a cellular band and may communicate with or receive a Subscriber Identity Module (SIM) card or other wireless network identifier. In other embodiments, other wireless data communication protocols, techniques, or methodologies may be used, including: radio frequency (RF) transmissions; IrDA (infrared); Bluetooth; ZigBee (and other variants of the IEEE 802.15 protocol); IEEE 802.11 (e.g., WiFi); IEEE 802.16 (WiMAX or any other variation); Direct Sequence Spread Spectrum; Near-Field Communication (NFC); Frequency Hopping Spread Spectrum; Long Term Evolution (LTE); cellular/wireless/cordless telecommunication protocols (e.g. 3G/4G, etc.); wireless home network communication protocols; paging network protocols; magnetic induction; satellite data communication protocols; wireless hospital or health care facility network protocols such as those operating in the WMTS bands; GPRS; proprietary wireless data communication protocols such as variants of Wireless USB; or any other suitable protocols, techniques, or methodologies for wireless communication.

The data store 440 is configured to store data generated and/or used by the breath analyte device 100. For example, the data store 440 may include breath acetone and hydrogen measurements made by the device 100. The data store 440 may include any of volatile memory elements (e.g., random access memory (RAM, such as DRAM, SRAM, SDRAM, and the like)), nonvolatile memory elements (e.g., ROM, hard drive, tape, CDROM, and the like), and combinations thereof. Moreover, the data store 440 may incorporate electronic, magnetic, optical, and/or other types of storage media.

The memory 450 may include any of: volatile memory elements (e.g., random access memory (RAM, such as DRAM, SRAM, SDRAM, etc.)), nonvolatile memory elements (e.g., ROM, hard drive, etc.), and combinations thereof. Moreover, the memory 450 may incorporate electronic, magnetic, optical, and/or other types of storage media. Note that the memory 450 may have a distributed architecture, where various components are situated remotely from one another, but can be accessed by the processor 410. The software in memory 450 can include one or more software programs, each of which includes an ordered listing of executable instructions for implementing logical functions.

In the example of FIG. 4, the software in the memory 450 includes an operating system (O/S) 460 and programs 470. The operating system 460 controls the execution of input/output interfaces 420 and provides scheduling, file and data management, memory management, communication control, and related services. The operating system 460 may be, for example, LINUX (or another UNIX variant) and any Linux-kernel-based operating systems, Raspbian, Ubuntu, OpenELEC, RISC OS, Arch Linux ARM, OSMC (formerly Raspbmc) and the Kodi open source digital media center, Pidora (Fedora Remix), Puppy Linux, Android (available from Google), Symbian OS, Microsoft Windows CE, Microsoft Windows 7 Mobile, iOS (available from Apple, Inc.), webOS (available from Hewlett Packard), Blackberry OS (Available from Research in Motion), and the like. The programs 470 may include various applications, add-ons, etc. configured to provide end user functionality such as customized control of one or more pumps 130, analyte sensors (e.g., acetone sensor 140 and hydrogen sensor 145), and/or sampling sensors 150.

Example Methods

Figure 5:
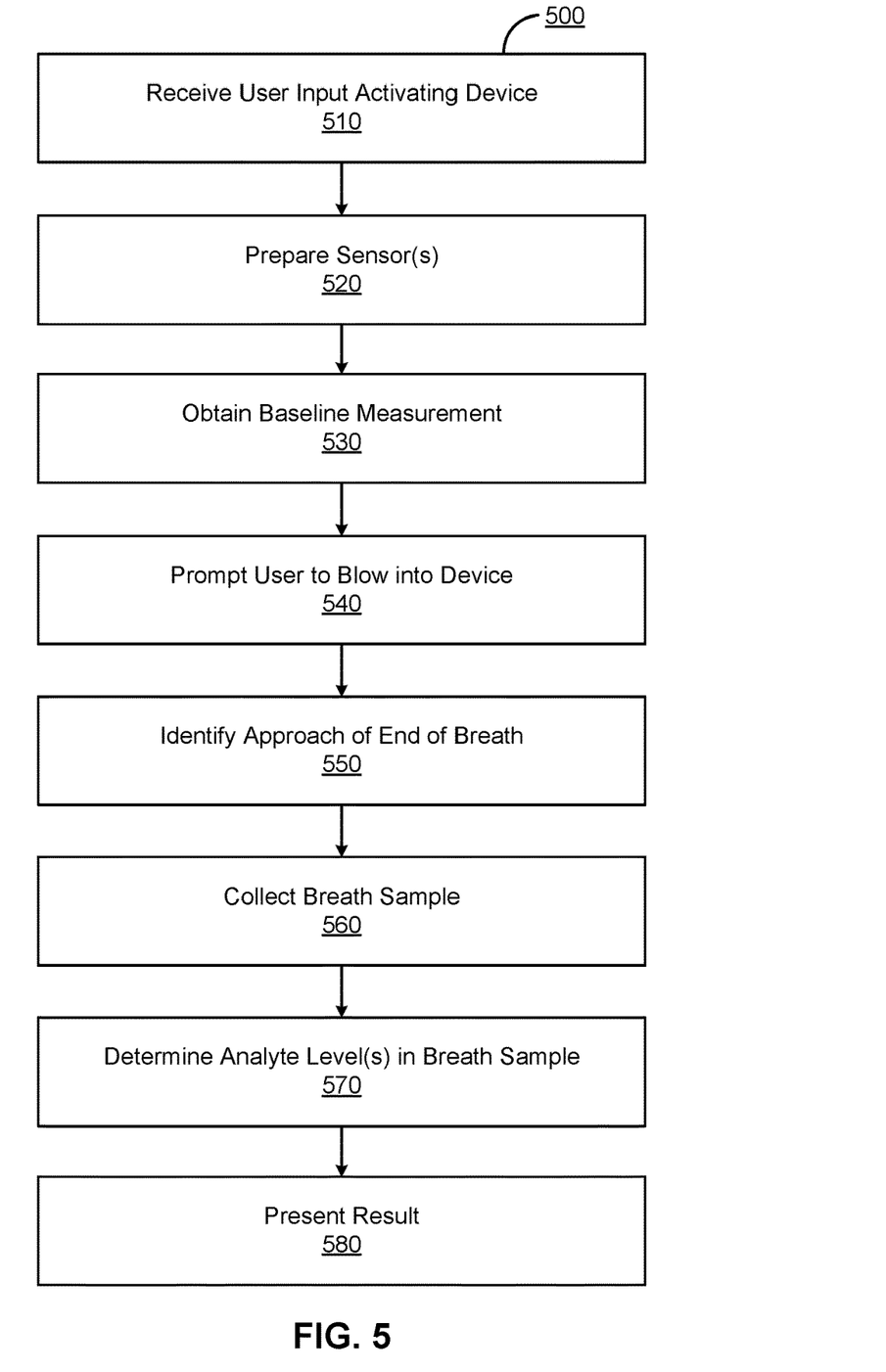
FIG. 5 is a flowchart illustrating a method of sampling a user's breath, according to one embodiment.

FIG. 5 illustrates a method 500 for sampling a user's breath, according to one embodiment. The steps of FIG. 5 are illustrated from the perspective of various components of the breath analyte device 100 performing the method 500. However, some or all of the steps may be performed by other entities or components. In addition, some embodiments may perform the steps in parallel, perform the steps in different orders, or perform different steps.

In the embodiment shown in FIG. 5, the method 500 begins with receiving 510 user input activating the device 100. For example, the user may begin the process by pressing the action button 220 to turn on or wake up the device 100. The control unit 160 prepares 520 one or more analyte sensors to take a measurement. This may include refreshing the acetone sensor 140 (e.g., by heating it to an elevated temperature) and/or heating it to its operating temperature. An example process for preparing 520 an acetone sensor 140 is described in greater detail below, with reference to FIG. 7. Electrochemical hydrogen sensors typically do not require preparation but may benefit by applying a bias voltage slightly higher than the operating bias and then reducing the applied voltage to an operating voltage prior to use.

Once the sensor or sensors are ready, the control unit 160 obtains 530 baseline readings from the sensors and prompts 540 the user to blow through the breath volume 110 (e.g., via an I/O interface 420 using a graphic, vibration, sound, or other indicator). The baseline may be a dynamic baseline (e.g., determined by averaging the sensor responses over a two second period). The control unit 160 identifies 550 the approaching end of breath of the user based on the output from the audio sensor 150. An example approach to identifying 550 the approaching end of breath of the user is described in greater detail below, with reference to FIG. 6.

Regardless of how the approaching end of breath is identified, the device 100 collects 560 a breath sample (e.g., by activating the pump 130 to pull the sample from the breath volume 110 into the flow cell 120). The control unit 160 determines 570 the level of one or more target analytes in the breath sample based on the output from the analyte sensor or sensors. For example, the control unit 160 may integrate the response of the analyte sensors 140 and 145 to the breath sample over a sample period and subtract the baseline levels for the acetone and hydrogen sensors to get a measurement of the concentration of acetone and hydrogen in the user's breath. The control unit 160 may also apply a drift correction term that accounts for changes in sensor behavior over time (e.g., due to wear and tear, etc.). The drift correction term may be calculated during calibration. In some embodiments, one or more metal-oxide analyte sensors may operate in a pulsed heating mode. This may provide additional information (e.g., to distinguish between sensor response due to acetone and distractors such as hydrogen). Alternately, the measured concentration of hydrogen may be used to modify the final measured acetone concentration.

The measurement may be presented 580 to the user (e.g., using a display I/O interface 420) and/or stored for later output (e.g., in the data store 440). Once the analyte level has been determined 570, the pump 130 may reactivate to clear the flow cell 120 and/or the control unit 160 may prepare 520 the acetone sensor 140 for another measurement.

Figure 6:
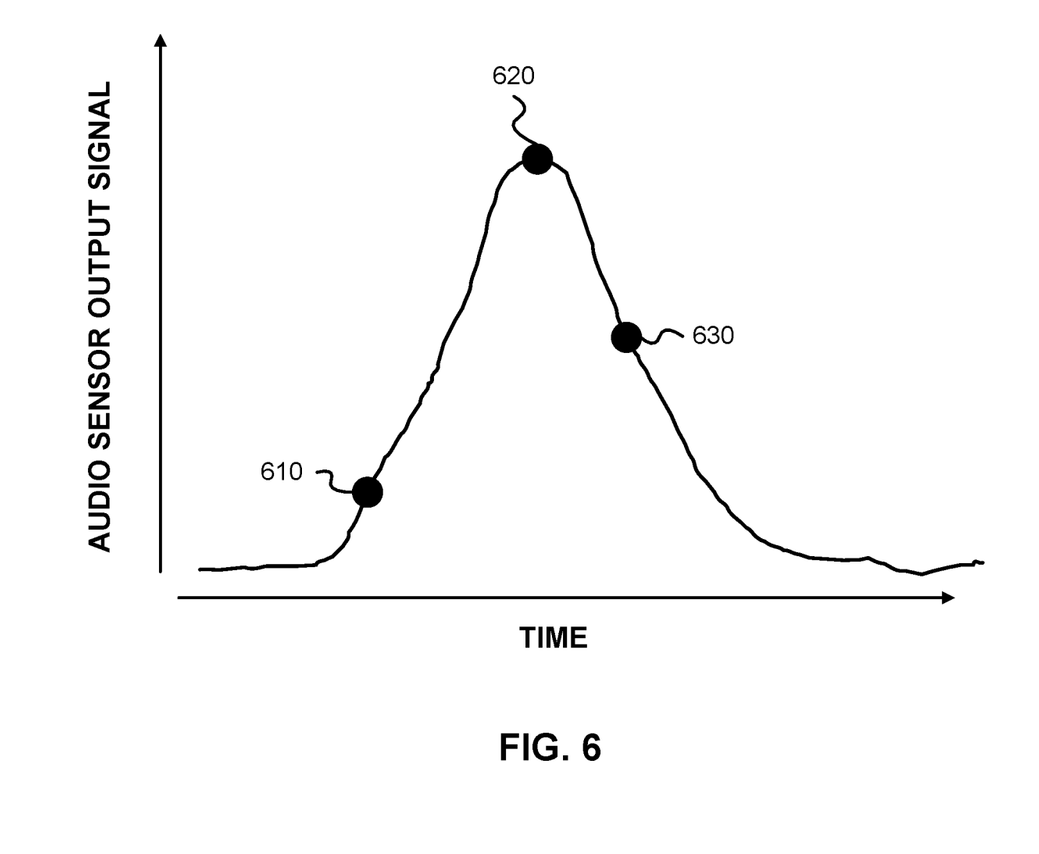
FIG. 6 is a graph illustrating the use of the output of an audio sensor for end-of-breath sampling, according to one embodiment.

FIG. 6 illustrates an example approach that uses an audio sensor 150 to detect the approaching end of a user's breath. As a user blows a full breath through the breath volume 110, the output of the audio sensor 150 first rises and then falls. When the signal stops rising and starts decreasing again, this indicates that the user is getting close to the end-of-breath.

Note that the average pressure within the breath volume 110 behaves similarly throughout a breath cycle.

In one embodiment, the control unit determines that a full breath is occurring when the output from the audio sensor 150 increases above a breath-detection threshold 610. The breath-detection threshold 610 may be set at a level such that ambient noise is unlikely to exceed it. Once the output increases above the breath-detection threshold 610, the control unit 160 monitors the output to identify the maximum 620. The maximum 620 may be identified by the output from the sensor consistently decreasing for a predetermined period (e.g., 0.1 seconds) and/or decreasing by more than a threshold amount (e.g., 90% of the previously observed maximum).

Figure 7:
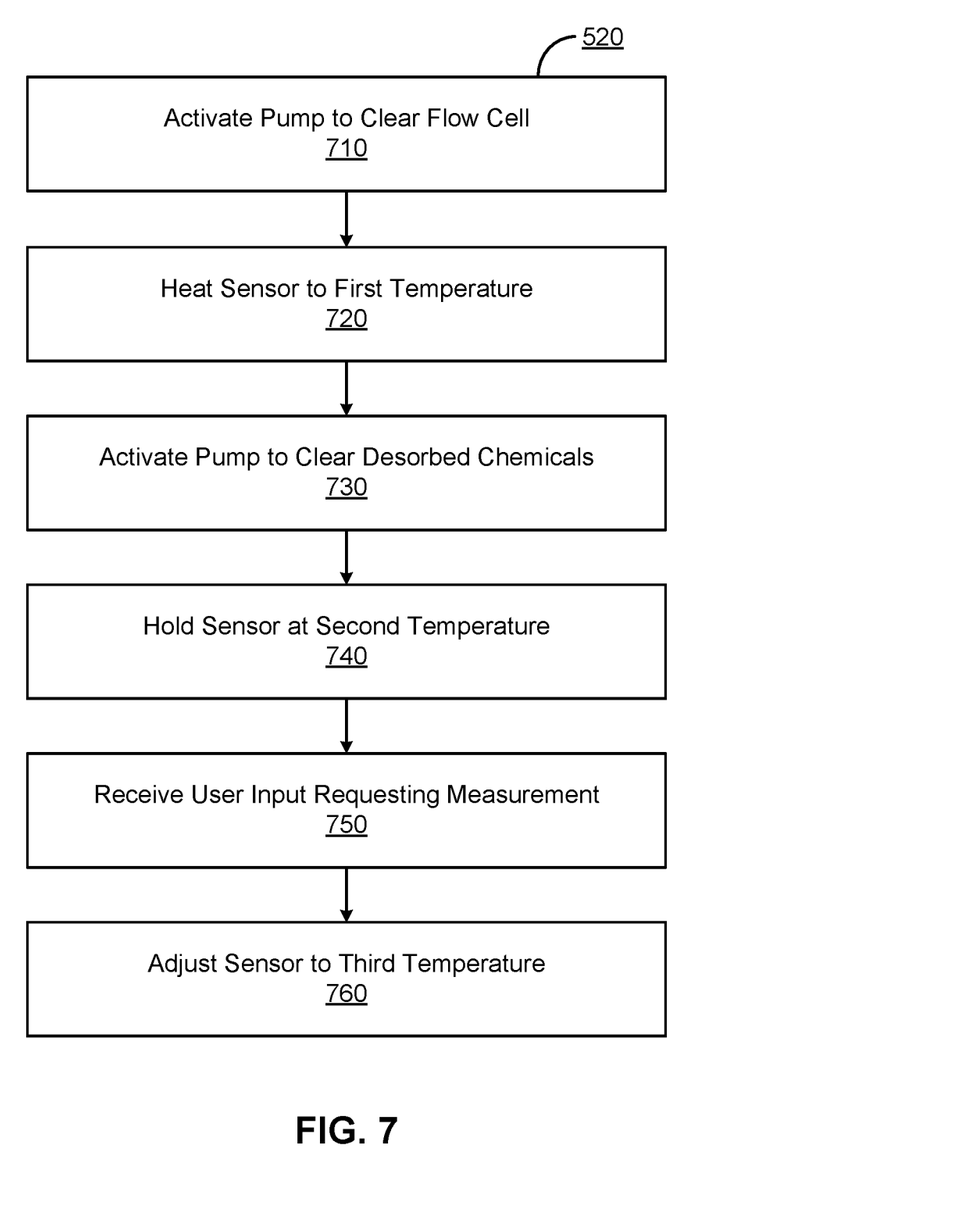
FIG. 7 is a flowchart illustrating a method of preparing a metal-oxide sensor, according to one embodiment.

Once the output drops below an end-of-breath threshold 630, the control unit 160 may trigger sampling of the user's breath (e.g., by activating the pump to pull a portion of the user's breath into the flow cell 120 and thus into contact with the acetone sensor 140). The end-of-breath threshold 630 may be set to any proportion of the maximum 620. In one embodiment, the end-of-breath threshold 630 is in the range from 75-98% of the maximum 620. In other embodiments, other end-of-breath thresholds 630 may be used FIG. 7 illustrates a method for preparing 520 a metal-oxide sensor (e.g., acetone sensor 140) for sampling, according to one embodiment. Metal oxide sensors (MOS) are composed of a catalytic metal-oxide coated onto a heating element. Heating the metal-oxide to high temperatures (e.g., 200-400 C) yields negatively charged oxygen species adsorbed at the metal-oxide active surface. These surface ions react with ambient target gases and release electrons into the metal-oxide film resulting in a change of electrical resistivity of the metal-oxide layer. Thus, the change of resistivity measured between two electrodes on the sensor 140 directly depends on the ambient target gas concentration. However, this is an inherently unstable system. The method shown in FIG. 7 can improve reliability and reproducibility of results by refreshing the sensor before a measurement is taken. The steps of FIG. 7 are illustrated from the perspective of various components of the breath acetone device 100 performing the method. However, some or all of the steps may be performed by other entities or components. In addition, some embodiments may perform the steps in parallel, perform the steps in different orders, or perform different steps.

In the embodiment shown in FIG. 7, the method begins by activating 710 the pump 130 to clear the flow cell 120. The control unit 160 heats 720 the sensor to a first temperature to burn off any adsorbed chemicals and generate negatively charged oxygen species at the active surface of the sensor 140. For example, the first temperature may be between 200 C and 500 C. The control unit 160 may activate 730 the pump 130 again (or it may remain pumping after step 710) to remove desorbed chemicals from the flow cell 120.

The control unit 160 holds 740 the sensor 140 at a second temperature that is sufficient to prevent significant adsorption of chemicals at the active surface. The second temperature may be the same or lower than the first temperature. For example, the second temperature may be between 150 C and 350 C. At this point, the control unit 160 may inform the user that the device 100 is ready to take a measurement (e.g., with a prompt on the display 210). If the device 100 remains in this state for more than a predetermined amount of time, the control unit 160 may abort the measurement and return the device 100 to a sleeping or off state. This prevents excessive battery use and potential damage to the device 100 that may arise from maintaining the sensor 140 at an elevated temperature.

Assuming the control unit 160 receives 760 user input requesting a measurement (e.g., the user pressing the action button 220), the temperature of the sensor 140 is adjusted 760 to a third temperature. The third temperature may be selected to optimize the response of the sensor 140 to acetone. For example, the third temperature may be between 200 C and 400 C. Once the sensor 140 reaches the third temperature, the device 100 may proceed with sampling the user's breath (e.g., as described previously with reference to FIG. 5).

Example Devices for Measuring Other Breath Analytes

As noted previously, while the above description focuses on measuring breath acetone and hydrogen, similar devices may be manufactured to detect other analytes in breath for various purposes. For example, Carbon monoxide (CO) is elevated in the exhaled breath of smokers and the concentration of CO can serve as a marker of smoking and smoking cessation. Similar to acetone, CO increases with the depth of an exhalation reaching an approximate steady-state close to the end-of-breath. In one embodiment, a breath CO device uses an electrochemical or fuel-cell sensor. Rather than use a heated catalytic element to oxidize the breath analyte as done by metal-oxide sensors, electrochemical sensors utilize a voltage bias between a catalytic or "working" electrode and a counter electrode to oxidize or reduce the gas analyte. A third electrode may be used in electrochemical CO sensors to maintain a substantially constant bias at the working electrode keeping the reaction rate and sensitivity of the sensor to CO constant. Many two- and three-electrode CO sensors may be used, including the NAP-505 and NAP-508 sensors from Nemoto, the EC4-500-CO sensor from SGX, and the FECS40-1000 sensor from Figaro.

One limitation of three-electrode CO sensors is a cross sensitivity to hydrogen which can be elevated in breath and make accurate measurements of CO in breath difficult. Therefore, in some embodiments, a CO breath device includes a four-electrode electrochemical sensor to reduce cross-sensitivity to hydrogen, such as the CO/CF-200-4E from Membrapor and the A3E/F from City Technology. These four-electrode sensors include an additional catalytic electrode that is sensitive to hydrogen but not CO, thus enabling the device to correct for the presence of hydrogen in the sample.

As another example, Hydrogen (H2) and methane (CH4) are generated by microbial fermentation of carbohydrates in the human bowel. This occurs when dietary carbohydrates are not absorbed in the small intestine and travel along the digestive tract into the large intestine. The generated hydrogen and methane are absorbed into the blood and subsequently emitted in the breath. The only source of hydrogen and methane in the breath is due to this mechanism. Because of this, hydrogen/methane breath tests can be used to detect carbohydrate maladsorption syndromes such as lactose, sucrose and/or fructose intolerance as well as diagnosing bacterial overgrowth of the small bowel (SIBO), a condition in which larger-than-normal numbers of colonic bacteria are present in the small intestine.

In one embodiment, a hydrogen/methane breath device includes a metal oxide sensor that shows selectivity to these gasses, such as the TGS821, TGS2611-C00, and TGS2611-E00 from Figaro and the SB-11A, 12A, and 12C from Nissha FIS. The device may also include a catalytic filter in front of the sensor to reduce the response to interfering analytes in breath. In another embodiment, the hydrogen/methane breath device includes an electrochemical sensor that can be used to measure H2 in breath, such as the 4YHT from City Technology and the H2/M-1000, H2/CA-1000, and H2/C-2000 from Membrapor. Another method of detecting methane in breath uses NDIR sensors which use infrared light absorption to selectively detect hydrocarbons in breath, such as the IR12BD from SGX.

As a further example, breath ammonia concentration is correlated with the presence of nitrogenous wastes such as urea in blood and therefore may be used as a method for monitoring hemodialysis and kidney function in patients with kidney disease. In one embodiment, a breath ammonia device includes a metal-oxide sensor, such as the TGS826 from Figaro and the MIC-5914 from SGX. In another embodiment, the breath ammonia device includes an electrochemical sensor, such as the SGX-4NH3 from SGX and the FECS44-100 from Figaro. One advantage of these electrochemical sensors is their inherent insensitivity to interferents in breath such as hydrogen and ethanol.

One of skill in the art will appreciate that detection devices may be constructed for other breath analytes by selecting an appropriate sensor. For example, using the principles disclosed, one could construct a breath measurement device for volatile sulfur compounds, isoprene, trimethylamine, or the like.

ADDITIONAL CONSIDERATIONS

Some portions of above description describe the embodiments in terms of algorithmic processes or operations. These operations, while described functionally, computationally, or logically, are understood to be implemented by computer programs including instructions for execution by a processor or equivalent electrical circuits, microcode, or the like.

As used herein, any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. It should be understood that these terms are not intended as synonyms for each other. For example, some embodiments may be described using the term "connected" to indicate that two or more elements are in direct physical or electrical contact with each other. In another example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments. This is done merely for convenience and to give a general sense of the disclosure. This description should be read to include one or at least one and the singular also includes the plural unless it is obvious that it is meant otherwise. Furthermore, where values are described as "approximate" or "substantially" (or their derivatives), such values should be construed as accurate +/−10% unless another meaning is apparent from the context. From example, "approximately ten" should be understood to mean "in a range from nine to eleven."

Upon reading this disclosure, those of skill in the art will appreciate still additional alternative structural and functional designs for a system and a process for measuring breath analyte levels. Thus, while particular embodiments and applications have been illustrated and described, it is to be understood that the described subject matter is not limited to the precise construction and components disclosed herein and that various modifications, changes and variations which will be apparent to those skilled in the art may be made in the arrangement, operation and details of the method and apparatus disclosed. The scope of protection should be limited only by the following claims.

What is claimed is:

1. A breath analyte device comprising:
    a pocketable, handheld housing having a length between five and twenty centimeters, a width between two and ten centimeters, and a depth between one and three centimeters;
    a breath volume within the housing;
    an input aperture fluidly connecting the breath volume to an exterior environment and configured for a user to blow a single breath into such that a portion of the single breath enters the breath volume;
    a sampling volume within the housing and in fluid communication with the breath volume;
    a microphone located within the housing in or adjacent to the breath volume and configured to generate a breath signal that varies in response to sound within the breath volume due to the single breath;
    an analyte sensor within the housing and in fluid communication with the sample volume, the analyte sensor configured to generate an analyte signal that varies in response to a concentration of an analyte present in the sampling volume; and
    a control unit, within the housing, communicatively coupled to the sampling sensor and the analyte sensor, the control unit comprising:
        a processor; and
        a computer-readable medium storing instructions that, when executed, cause the processor to:
            identify a sample time for the single breath using the breath signal; and
            at the sample time, measure the concentration of the analyte in the sampling volume based on the analyte signal.

2. The breath analyte device of claim 1, wherein the instructions that cause the processor to identify the sample time comprise instructions that cause the processor to:
    detect the breath signal increasing above a breath-detection threshold due to the single breath;
    responsive to the breath signal increasing above a breath-detection threshold, identify a maximum in the breath signal due to the single breath, the maximum being after the breath signal increased above the breath-detection threshold; and responsive to identifying the maximum in the breath signal, identify an end-of-breath point at which the breath signal drops below an end-of-breath threshold due to the single breath, the end-of-breath point being after the maximum in the breath signal, wherein the sample time corresponds to the end-of-breath point.

3. The breath analyte device of claim 2, wherein the instructions that cause the processor to identify the maximum in the breath signal comprise instructions that cause the processor to detect the breath signal decreasing for a predetermined period by more than a maximum-detection threshold amount.

4. The breath analyte device of claim 1, further comprising a pump in fluid communication with the sampling volume and configured to motivate gas from the breath volume into the sampling volume.

5. The breath analyte device of claim 4, wherein the instructions, when executed, further cause the processor to activate the pump prior to measuring the concentration of the analyte in the sampling volume.

6. The breath analyte device of claim 4, wherein the pump is connected to the sampling volume via a pump conduit and configured to pull gas from the sampling volume.

7. The breath analyte device of claim 1, wherein the housing is a unitary enclosure.

8. The breath analyte device of claim 1, wherein the first analyte is acetone.

9. The breath analyte device of claim 1, wherein the analyte sensor is a metal-oxide sensor.

10. The breath analyte device of claim 1, further comprising a display, wherein the instructions further comprise instructions that cause the processor to:
    activate a pump one or more times to remove fluid from the sampling volume prior to the concentration of the analyte in the sampling volume being measured;
    determine that the analyte sensor is ready to measure the concentration of the analyte; and
    display an indication to the user on the display that the analyte sensor is ready to measure the concentration of the analyte.

11. The breath analyte device of claim 1, further comprising a display, wherein the instructions further comprise instructions that, when executed, cause the processor to instruct the display to present a prompt to the user to blow into the breath volume.

12. The breath analyte device of claim 11, wherein the instructions further comprise instructions that, when executed, cause the processor to instruct the display to present the measured concentration of the target analyte to the user.

13. The breath analyte device of claim 1, wherein the instructions that cause the processor to measure the concentration of the analyte in the sampling volume comprise instructions that, when executed, cause the processor to:
    integrate the analyte signal over a sample period; and
    subtract, from the integrated analyte signal, one or more of a baseline level or a drift correction to obtain the concentration of the analyte.

14. The breath analyte device of claim 1, further comprising a second analyte sensor within the housing and in fluid communication with the sample volume, the second analyte sensor configured to generate a second analyte signal that varies in response to a concentration of a second analyte present in the sampling volume, wherein the instructions, when executed, further cause the processor to measure the concentration of the second analyte in the sampling volume based on the second analyte signal.

15. A method for measuring concentration of a breath analyte, the method comprising:
    receiving, in a breath volume within a pocketable hand-held device, gas exhaled by a user in a single breath;
    receiving, from a microphone, a breath signal that varies in response to sound in the breath volume due to the single breath;
    identifying a sample time for the single breath using the breath signal;
    receiving, from an analyte sensor, an analyte signal that varies in response to a concentration of an analyte present in a sampling volume; and
    measuring, for a time period starting at the sample time, the concentration of the first and analyte in the sampling volume using the signal.

16. The method of claim 15, wherein identifying the sample time comprises:
    detecting the breath signal increasing above a breath-detection threshold due to the single breath;
    responsive to the breath signal increasing above the breath-detection threshold, identifying a maximum in the breath signal due to the single breath, the maximum being after the breath signal increased above the breath-detection threshold; and
    responsive to identifying the maximum in the breath signal, identifying an end-of-breath point for the single breath at which the breath signal drops below an end-of-breath threshold due to the single breath, the end-of-breath point being after the maximum in the breath signal, wherein the sample time corresponds to the end-of-breath point.

17. The method of claim 16, wherein the end-of-breath threshold is in a range from 75% to 98% of the maximum in the breath signal due to the single breath.

18. The method of claim 15, further comprising:
    receiving user input indicating a measurement of breath analyte is desired;
    preparing the analyte sensor to take the measurement responsive to the user input;
    displaying, once the analyte sensor is ready to take the measurement, a prompt to the user to blow into the breath volume; and
    displaying an indication of the breath analyte level to the user.

19. The method of claim 14, further comprising pumping a portion of the gas exhaled by the user from the breath volume to the sample volume prior to measuring the concentration of the analyte in the sampling volume.

20. A non-transitory computer-readable medium storing instructions that, when executed by a pocketable hand-held breath analyte device, cause the pocketable hand-held breath analyte device to perform operations comprising:
    receiving, in a breath volume within a pocketable hand-held device, gas exhaled by a user in a single breath;
    receiving, from a microphone, a breath signal that varies in response to sound in the breath volume due to the single breath;
    identifying a sample time for the single breath using the breath signal;
    receiving, from an analyte sensor, an analyte signal that varies in response to a concentration of an analyte present in a sampling volume; and measuring, for a time period starting at the sample time, the concentration of the analyte in the sampling volume using the analyte signal.

\* \* \* \* \*

UNITED STATES PATENT AND TRADEMARK OFFICE
CERTIFICATE OF CORRECTION

PATENT NO. : 11,730,391 B2
APPLICATION NO. : 17/851792
DATED : August 22, 2023
INVENTOR(S) : Ratto et al.

It is certified that error appears in the above-identified patent and that said Letters Patent is hereby corrected as shown below:

On the Title Page

Item "(*)", in Column 1, in "Notice", Line 3, below "U.S.C. 154(b) by 0 days." insert -- This patent is subject to a terminal disclaimer. --.

In the Claims

In Column 15, in Claim 8, Line 29, after "wherein the" delete "first".

In Column 16, in Claim 15, Line 18, after "of the" delete "first and".

In Column 16, in Claim 15, Line 19, after "using the" insert -- analyte --.

In Column 16, in Claim 19, Line 50, delete "claim 14," and insert -- claim 15, --, therefor.

Signed and Sealed this
Fifth Day of March, 2024

Katherine Kelly Vidal
*Director of the United States Patent and Trademark Office*